(12) United States Patent
Moussy et al.

(10) Patent No.: US 6,497,729 B1
(45) Date of Patent: *Dec. 24, 2002

(54) IMPLANT COATING FOR CONTROL OF TISSUE/IMPLANT INTERACTIONS

(75) Inventors: Francis Moussy, Farmington, CT (US); Donald Kreutzer, Avon, CT (US); Diane Burgess, Storrs, CT (US); Jeffrey Koberstein, Mansfield, CT (US); Fotios Papadimitrakopoulos, Coventry, CT (US); Samuel Huang, Bloomfield, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,857

(22) Filed: Nov. 19, 1999

Related U.S. Application Data
(60) Provisional application No. 60/109,289, filed on Nov. 20, 1998.

(51) Int. Cl.[7] .................................................. A61F 2/02
(52) U.S. Cl. ............................... 623/23.57; 623/11.11; 424/423
(58) Field of Search ........................... 623/11.11, 23.57, 623/23.71, 23.73; 424/423; 600/365, 377

(56) References Cited

U.S. PATENT DOCUMENTS 3,773,919 A    11/1973   Boswell et al.

(List continued on next page.)

FOREIGN PATENT DOCUMENTS

| EP | 0 554 955 A1 | 8/1993 |
|---|---|---|
| EP | 0 656 215 A1 | 1/1994 |
| WO | WO 91/01680 | 2/1991 |
| WO | WO 93/08766 | 5/1993 |
| WO | WO 97/19344 | 5/1997 |
| WO | WO 97/46267 | 12/1997 |

OTHER PUBLICATIONS

M. Tsung and D.J. Burgess, "Preparation and Stabilization of Heparin/Gelatin Complex Coacervate Microcapsules" in Journal of Pharmaceutical Sciences., vol. 86, No. 5 pp. 603–607, (May 1977).

C. Grandils, et al., "Preparation of poly (d,l) lactide microspheres by emulsion–solvent evaporation, and their clinical applications as a convenient embolic material" in Journal of Biomedical Materials Research, vol. 26, pp. 467–479 (1992).

Heya et al., "In Vitro and in Vivo Evaluation of Thyrotrophin Releasing Hormone Release from Copoly (dl–lactic/glycolic acid)Microspheres" in Journal of Pharmaceutical Sciences, vol. 83, No. 5, pags. (6360640 (May 1994).

Muhlhauser et al. "VEGF 165 Expressed by a Replication–Deficient Recombinant adenovirus Vector Induces Angiogenesis in Vivo" in Circulation Research vol. 77, pp. 1077–1086 (1995).

*Primary Examiner*—Paul B. Prebilic
(74) *Attorney, Agent, or Firm*—Cantor Colburn LLP (57) ABSTRACT

A tissue/implant interface, comprising an implant and a bioactive polymer layer adjacent at least a portion of the outer surface of the implant, wherein the polymer layer contains at least one tissue response modifier covalently attached to the polymer layer or entrapped within the polymer layer in a quantity effective to control the tissue response at the site of implantation. Preferably, the at least one tissue response modifier controls inflammation, fibrosis, and/or neovascularization. Exemplary tissue response modifiers include, but are not limited to, steroidal and non-steroidal anti-inflammatory agents, anti-fibrotic agents, antiproliferative agents, cytokines, cytokine inhibitors, neutralizing antibodies, adhesive ligands, and combinations thereof. Use of the various combinations of tissue response modifiers with bioactive polymers provides a simple, flexible and effective means to control the implant/tissue interphase, improving implant lifetime and function.

43 Claims, 5 Drawing Sheets

U.S. PATENT DOCUMENTS

| | | | |
|---|---|---|---|
| 3,921,636 A | * 11/1975 | Zaffaroni | 128/260 |
| 4,122,605 A | 10/1978 | Hirabayashi et al. | |
| 4,130,639 A | 12/1978 | Shalaby et al. | |
| 4,155,992 A | 5/1979 | Schmitt | |
| 4,186,189 A | 1/1980 | Shalaby et al. | |
| 4,304,591 A | 12/1981 | Mueller et al. | |
| 4,379,138 A | 4/1983 | Pitt et al. | |
| 4,648,880 A | 3/1987 | Brauman | |
| 4,900,556 A | 2/1990 | Wheatley et al. | |
| 4,983,181 A | 1/1991 | Civerchia | |
| 4,994,081 A | 2/1991 | Civerchia et al. | |
| 5,271,961 A | * 12/1993 | Mathiowitz et al. | 427/213.31 |
| 5,342,622 A | 8/1994 | Williams et al. | |
| 5,401,508 A | * 3/1995 | Manesis | 424/427 |
| 5,562,922 A | 10/1996 | Lambert | |
| 5,593,697 A | 1/1997 | Barr et al. | |
| 5,656,297 A | * 8/1997 | Bernstein et al. | 424/427 |
| 5,705,178 A | 1/1998 | Roufa et al. | |
| 5,779,734 A | 7/1998 | Ledergerber | |
| 5,798,115 A | 8/1998 | Santerre et al. | |
| 5,801,033 A | 9/1998 | Hubbell et al. | |
| 5,932,539 A | * 8/1999 | Stupp et al. | 514/2 |
| 5,973,089 A | * 10/1999 | Meijs et al. | 526/247 |

* cited by examiner

IMPLANT COATING FOR CONTROL OF TISSUE/IMPLANT INTERACTIONS

CROSS-REFERENCE TO RELATED APPLICATION

This application claims priority to U.S. Provisional Application No. 60/109,289, filed Nov. 20, 1998, which is incorporated by reference herein in its entirety.

STATEMENT REGARDING FEDERALLY SPONSORED RESEARCH & DEVELOPMENT

This invention was made with Government support under Grant Number 1RO1RR14171 awarded by the National institutes of Health. The Goverment has certain rights in the invention.

BACKGROUND OF THE INVENTION

1. Field of the Invention

This invention relates generally to the field of implants for human and animal bodies. In particular, this invention relates to apparatus and methods for controlling tissue/implant interactions, thereby allowing better integration, function, and extended lifespan of implants in the body.

2. Description of the Related Art

Implantable artificial materials and devices, such as drug delivery systems, pacemakers, artificial joints, and organs play an important role in health care today. In addition to these devices, implantable monitoring devices or "biosensors" have great potential for improving both the quality of care and quality of life of patients and animals. An exemplary monitoring device that would greatly improve the quality of life for diabetic patients and animals, for example, is an implantable glucose monitor for the pain-free, continuous, reliable monitoring of blood glucose levels. Diabetic patients presently monitor their own glucose blood levels by obtaining samples of capillary blood through repeated finger-pricking. Because the tests are painful, time-consuming, and must be performed multiple times throughout a single day, diabetic patients resist performing an adequate number of daily tests. This low compliance exacerbates the intrinsically discontinuous nature of the monitoring, and ultimately leads to the extensive pathology associated with diabetic patients.

One of the major problems associated with all types of implants is biocompatibility of the implant with the body, and in particular with the tissue adjacent to the site of the implant. For example, despite attempts to design implantable biosensors for glucose and other monitoring functions, none developed to date provide pain-free, reliable and continuous monitoring. One reason is that current implantable sensors suffer from a progressive loss of function after relatively short periods of time in vivo. This loss in function arises from multiple factors, some of the most important of which include protein adsorption, inflammation, and fibrosis (encapsulation) resulting from tissue trauma at the site of the implant. This fibrosis results in loss of blood vessels at the site of implantation and therefore in a reduced access to blood glucose levels. These factors can also interfere with the function of other implants and implantable devices, such as insulin pumps, pacemakers, artificial joints, and artificial organs.

One approach to control the inflammation and fibrosis resulting from tissue trauma at the site of implantation has been to use inert materials such as titanium or single-crystalline alumina, as disclosed in U.S. Pat. No. 4,122,605 to Hirabayashi et al. While suitable for bone or tooth implants, this approach is not useful in more complex prosthetic devices or in biosensors, which requires use of a variety of materials. Another approach has been the use of a porous, outer coating of DACRON or TEFLON, as disclosed in U.S. Pat. No. 4,648,880 to Brauman et al., or with polytetrafluorethylene, as disclosed in U.S. Pat. No. 5,779,734. While suitable for prostheses such as breast implants, such coatings are not practical for prosthetic devices or biosensors having complex geometries. The most commonly-used approach to control tissues responses, particularly inflamation, has been the systemic administration of drugs such as corticosteroids. Such systemic administration can result in side effects such as generalized immunosupression, bloating, and psychiatric problems, especially over the long term. There accordingly remains a need in the art for apparatus and methods for controlling tissue/implant interactions, particularly for implantable materials, prostheses, and devices such as biosensors.

SUMMARY OF THE INVENTION

The above-discussed and other drawbacks and deficiencies of the prior art are overcome or alleviated by an improved tissue/implant interface, comprising an implant having an outer surface and a bioactive polymer layer adjacent to at least a portion of the outer surface of the implant. In a preferred embodiment, the polymer layer contains at least one tissue response modifier covalently attached to the polymer layer or entrapped within the polymer layer in a quantity effective to control the tissue response at the site of implantation. The bioactive polymer layer may be a synthetic organic polymer such as a hydrogel, or a natural polymer such as a protein. The polymer may also be self-assembled. Preferably, the at least one tissue response modifier controls inflammation, fibrosis, cell migration, cell proliferation, leukocyte activation, leukocyte adherence, lymphocyte activation, lymphocyte adherence, macrophage activation, macrophage adherence, cell death and/or neovascularization. Exemplary tissue response modifiers include, but are not limited to, steroidal and non-steroidal anti-inflammatory agents, anti-fibrotic agents, anti-proliferative agents, cytokines, cytokine inhibitors, neutralizing antibodies, adhesive ligands, metabolites and metabolic intermediates, DNA, RNA, cytotoxic agents, and combinations thereof. The tissue response modifiers may be covalently attached to the polymer layer or entrapped within the polymer layer.

In another embodiment, the tissue response modifier is covalently attached to the polymer layer or entrapped within the polymer layer in slow-release form, for example in the form of biodegradable polymers, nanoparticles, liposomes, emulsions, and microspheres, to provide long-term delivery of the tissue response modifier to the site of implantation.

The addition of the various combinations of tissue response modifiers with bioactive polymers provides an extremely simple, flexible and effective means to control the implant/tissue interphase, improving implant lifetime and function. The above-discussed and other features and advantages will be appreciated and understood by those skilled in the art from the following detailed description and drawings.

BRIEF DESCRIPTION OF THE DRAWINGS

Referring now to the drawings wherein like elements are numbered alike in the several FIGS.

DETAILED DESCRIPTION OF THE PREFERRED EMBODIMENTS

As used herein, "implant" refers broadly to any material or device which is invasively inserted within the body of a vertebrate, e.g., bird, reptile, amphibian, or mammal. The improved tissue/implant interface of the present invention comprises, in a first embodiment, an implant having an outer surface and a bioactive polymer layer adjacent to at least a portion of the outer surface of the implant, wherein the polymer layer contains at least one tissue response modifier covalently attached to the polymer layer or entrapped within the polymer layer in a quantity effective to control the tissue response at the site of implantation. The at least one tissue response modifier serves to modify tissue response to the implant at the site of implantation, moderating or preventing the tissue responses which lead to implant rejection, impairment, or loss of function.

"Tissue response modifiers" as used herein are factors that control the response of tissue adjacent to the site of implantation. One facet of this response can be broadly divided into a two-step process, inflammation and wound healing. An uncontrolled inflammatory response (acute or chronic) results in extensive tissue destruction and ultimately tissue fibrosis. Wound healing includes regeneration of the injured tissue, repair (fibrosis), and ingrowth of new blood vessels (neovascularization and angiogenesis). For fibrosis, the body utilizes collagen from activated fibroblasts to "patch and fill" the unregenerated areas resulting from trauma and inflammation. Ingrowth of new blood vessels is critical to the ultimate outcome of wound healing. A number of other responses are also included within this category, for example fibroblast formation and function, leukocyte activation, leukocyte adherence, lymphocyte activation, lymphocyte adherence, macrophage activation, macrophage adherence, thrombosis, cell migration, cell proliferation including uncontrolled growth, neoplasia, and cell injury and death. Adverse tissue responses to implantation may also arise through genetic disorders, immune diseases, infectious disease, environmental exposure to toxins, nutritional diseases, and diseases of infancy and childhood.

Tissue response modifiers are therefore a broad category of organic and inorganic, synthetic and natural materials, and derivatives thereof which affect the above responses to tissue injury upon implantation. Such materials include but are not limited to synthetic organic compounds (drugs), peptides, polypeptides, proteins, lipids, sugars, carbohydrates, certain RNA and DNA, and fatty acids, as well metabolites and derivatives of each. Tissue response modifiers may also take the form of, or be available from genetic material, viruses, prokaryotic or eukaryotic cells. The tissue response modifiers can be in various forms, such as unchanged molecules, components of molecular complexes, or pharmacologically acceptable salts or simple derivatives such as esters, ethers, and amides. Tissue response modifiers may be derived from viral, microbial, fungal, plant, insect, fish, and other vertebrate sources.

Exemplary tissue response modifiers include, but are not limited to, anti-inflammatory agents such as steroidal drugs, for example corticosteroids such as Dexamethasone (9-alpha-fluoro-16-alpha-methylprednisolone), a potent, broad spectrum steroidal anti-inflammatory and anti-fibrotic drug with known efficacy in a diabetic rat model, and methyl prednisone, triamcoline (fluoroxyprednilisone), hydrocortisone (17-hydroxycorticosterone), and analogs thereof, and non-steroidal drugs, for example Ketoprofin (2-(3-benzophenyl)propionic acid), cyclosporin, Naproxin ((+)-6-methoxy-α-methyl-2-naphthalene acetic acid), and Ibuprofin (4-isobutyl-α-methylphenyl acetic acid).

Other exemplary tissue response modifiers include neovascularization agents such as cytokines. Cytokines are growth factors such as transforming growth factor alpha (TGFA), epidermal growth factor (EGF), vascular endothelial growth factor (VEGF), and anti-transforming growth factor beta (TGFB). TGFA suppresses collagen synthesis and stimulates angiogenesis. It has been shown that epidermal growth factor tethered to a solid substrate retains significant mobility and an active conformation. VEGF stimulate angiogenesis, and is advantageous because it selectively promotes proliferation of endothelial cells and not fibroblasts or collagen synthesis, in contrast to other angiogenic factors. In addition to promoting would healing, the improved blood flow resulting from the presence of neovascularization agents should also improve the accuracy of sensor measurements.

Another type of tissue response modifier is neutralizing antibodies including, for example, anti-transforming growth factor beta antibody (anti-TGFB); anti-TGFB receptor antibody; and anti-fibroblast antibody (anti-CD44). Anti-TGFB antibody has been shown to inhibit fibroblast proliferation, and hence inhibit fibrosis. Because of the importance of TGFB in fibrosis, anti-TGFB receptor antibodies inhibit fibrosis by blocking TGFB activation of fibroblasts. Recent studies have demonstrated that anti-CD44 antibody induces programmed cell death (apoptosis) in fibroblasts in vitro. Thus, use of anti-CD44 antibody represents a novel approach to inhibition of fibroblast formation, and therefore fibrosis. Other anti-proliferative agents include Mitomicyin C, which inhibits fibroblast proliferation under certain circumstances, such as after vascularization has occurred.

Adhesive ligands ("binding motifs") may also be used as tissue response modifiers, wherein the adhesive ligands are incorporated into the polymer layer to stimulate direct attachment of endothelial cells to implant surfaces. Such attachment promotes neovascularization at the implant/tissue interface. Where the surface density of binding motifs has an effect on the cellular response, variation in the density of the binding motifs allows control of the response. Exemplary adhesive ligands include but are not limited to the arginine-glycine-aspartic acid (RGD) motif, and arginine-glutamic acid-aspartic acid-valine (REDV) motif, a fibronectin polypeptide. The REDV ligand has been shown to selectively bind to human endothelial cells, but not to bind to smooth muscle cells, fibroblasts or blood platelets when used in an appropriate amount.

The at least one tissue response modifier is covalently bound to or entrapped within at least one bioactive polymer layer. As used herein, a "bioactive" polymer layer is one which can control (enhance or suppress) tissue reactions to implanted materials.

The bioactive polymers are generally biocompatible, that is, physiologically tolerated and not causing adverse local or systemic responses. It is to be understood that the term "layer" as used herein is inclusive of blocks, patches, semicircles, and other geometries without limitation. While synthetic polymers such as poly(tetrafluoroethylene), silicones, poly(acrylate), poly(methacrylate), hydrogels, and derivatives thereof are most commonly used, natural polymers such as proteins and carbohydrates are also within the scope of the present invention. The bioactive polymer layer functions to protect the implant and preserve its function, minimize protein adsorption of the implant, and serve as a site for the delivery of the tissue response modifiers or drug delivery vehicles.

In one embodiment, the tissue response modifiers are entrapped or covalently bound within a hydrogel. Hydrogels are formed from the polymerization of hydrophilic and hydrophobic monomers to form gels and are described, for example, in U.S. Pat. Nos. 4,983,181 and 4,994,081, which are incorporated by reference herein. They consist largely of water, and may be crosslinked by either chemical or physical methods. Chemical crosslinking is exemplified by the free-radical induced crosslinking of dienes such as ethylene glycol dimethacrylate (EGDMA), and the like. Physical crosslinks are formed by copolymerizing a hydrophobic co-monomer with the water-soluble monomer, and then by contacting the copolymerized gel with water. Physical association of the hydrophobic regions of the gel results in the formation of physical crosslinks. Control of the ratio of hydrophilic to hydrophobic monomers allows control of the final properties of the gel. Highly water-swollen hydrogels are bioactive, and have minimal impact on the diffusion rates of small molecules. Hydrogels are also intrinsically mobile, and therefore have minimal deleterious effects on associated peptide tissue response modifiers.

Hydrogels may be formed by the polymerization of monomers such as 2-hydroxyethyl methacrylate, 2-hydroxyethyl methacrylate, fluorinated acrylated, acrylic acid, and methacrylic acid, and combinations thereof. Preferred hydrogels are copolymers of 2-hydroxyethyl methacrylate, wherein the co-monomers are selected to improve mechanical strength, stability to hydrolysis, or other mechanical or chemical characteristics. Preferred co-monomers include, but are not limited to, 3-hydroxypropyl methacrylate, N-vinyl pyrrolidinone, 2-hydroxyethyl acrylate, glycerol methacrylate, n-isopropyl acrylamide, N,N-dimethylacrylamide, glycidyl methacrylate, and combinations thereof. Particularly preferred hydrogels are terpolymers of 2-hydroxyethyl meth-acrylate (HEMA), N-vinyl pyrrolidinone (NVP), and 2-N-ethylperflourooctanesulfanamido ethyl acrylate (FOSA) with added EGDMA to provide controlled crosslinking. HEMA is hydrophilic, and swells in the presence of water. The hydroxyl groups of HEMA also provide potential sites for the covalent attachment of tissue response modifiers, slow release delivery systems, and the like. Acrylic acid, methacrylic acid, and other functionalized vinyl monomers can also be employed to provide these attachment sites. NVP is amphiphilic, wherein the backbone ring provides hydrophobicity and the polar amide group provides hydrophilicity. Poly(vinyl pyrrolidinone) is water soluble, physiologically inactive, and forms complexes with a number of small molecules such as iodine and chlorhexidine. Use of NVP improves the toughness of polymerized HEMA, and provides for the enhanced solubility of the other monomers under bulk polymerization conditions.

Polymerization methods known in the art may be used, depending on the implant. Thus, for implants capable of tolerating increased temperatures, polymerization may be initiated by heat in the presence of initiator such as azobisisobutyronitrile (AIBN). Photoinitiation by UV light may be used in the presence of initiators such as benzoin or benzil, and by visible light in the presence of initiators such as Eosin. Binding of the hydrogel to the implant may be by mechanical forces, as the sheath around the implant formed during preparation of the hydrogel shrinks considerably during polymerization.

In still another preferred embodiment, the tissue response modifiers are associated with a bioactive polymer layer which is generated by supramolecular self-assembly. Generation of materials by self-assembly has resulted in significant advances in the area of thin films, for example, wherein the sequential layering of (poly)cations/(poly)anions has allowed the incorporation of molecular dyes, nanocrystals, microspheres, charged proteins, and cell-growth factors into larger structures. Such layer-by-layer growth of small and large molecular weight compounds offers a high degree of flexibility in the construction of these more complex structures.

Electrostatic self-assembly is based on the attraction of oppositely charged species that render the "complex" insoluble to the mother solutions. This technique offers a powerful tool for building a variety of layer and multilayer structures from poly(anions) and poly(cations). These "fuzzy" nanoassemblies exhibit significant intermixing of the opposite charged polyion chains. The strong metal-ligand forces that stabilize self-assemblies give rise to physically-crosslinked structures. These systems are very stable even at low pH and in polar solvents, eliminating the need for chemical-crosslinking to provide dimensional stability. Assembly may occur directly on the implant, or adjacent a hydrogel membrane, providing a greater number of options for the development of the membranes and interactive surface hydrogels. The layer thickness and other microstructural characteristics of these assemblies are sensitive to the type of charged species, their concentration, pH, molecular weight, ionic strength and the like.

An example of a bioactive layer generated by self-assembly is the formation of NAFION™/$Fe^{3+}$ multilayer films. NAFION™ is a perfluorinated electrolyte having sulfonic acid functionalities which has been previously used as a semipermeable membrane for electrochemical sensors. However, the strong ion-exchange properties of NAFION™ lead to calcification in vitro and in vivo. The sulfonate ($R-SO_3$) groups present in the hydrophilic domains of the membrane act as nucleating sites for deposition of calcium phosphate. These crystals tend to inhibit metabolite transport through the membrane, and also embrittle the membrane, causing it to crack.

Electrostatic assembly of NAFION™ and $Fe^{3+}$ from dilute solutions of ferric citrate at a pH in the range rom about 2 to about 6 can be used to prevent calcium deposition. Layer-by-layer assembly allows gradual stress relaxation and complete substitution of NAFION's protons with $Fe^{3+}$, thus inactivating all of the calcification nucleation sites. Use of ferric citrate solutions at a mild pH (e.g., at about 6) allows assembly of the membranes without protein, enzyme, or other tissue response modifier inactivation. Accordingly, upon immersion into the acidic NAFION™ solution (pH about 3), substrate hydroxyl groups, i.e., silanol groups (Si—OH) are partially protonated, providing a strong electrostatic force to attract the negatively charged NAFION™ micelles. After rinsing in water to remove loosely bounded species, the substrate is dipped into ferric chloride solution. Ferric ions are attracted by the sulfonate groups, facilitating the surface charge reversal thereby restoring the original surface charge. The entire process is repeated till the desired thickness is achieved.

Another poly(ligand) useful for self-assembly is the mussel adhesive protein (MAP). Self-assembly of biological materials such as mussel adhesive proteins allows the incorporation of materials which improve implant biocompatibility. MAP produced by the blue seal mussel (*Mytilus edulis*) generally comprises 75 to 85 repeating decameric units having the primary sequence of KPSY-Hyp-Hyp-T-DOPA, wherein Hyp is hydroxyproline and DOPA is 3,4-dihydroxyphenylalanine. DOPA is a strong metal chelating agent, particularly with $Ca^{2+}$ and $Fe^{3+}$, and the strong self-aggregation of DOPA in the presence of cations results in supra-molecular self-assembly. Accordingly, a substrate comprising metal chelating groups, for example free amine groups, is sequentially immersed first, in a solution comprising metal ions (i.e. $Ca^{2+}$ and/or $Fe^{3+}$) (followed by optional washing in fresh solvent); and second, in a solution comprising the poly(ligand) (i.e. the MAP protein) (followed by optional washing in fresh solvent). The thickness of the membrane will be directly proportional to the number of sequential immersion cycles. The assembly of the membrane is monitored with Variable Angle Spectroscopic Ellipsometry (VASE), UV-VIS and Quartz Crystal Microbalance. The strong chelation between $Ca^{2+}$ and DOPA in the MAP membrane results in a substantial decrease in porosity, allowing the permeation of small molecules such as glucose and oxygen, while excluding permeation of larger molecules. Additionally, the introduction of small amount of crosslinking, via the Michael addition from neighboring lysine repeats by slight increase of pH above 8.5, may be used to further fine-tune the permeability of such assemblies to levels.

A major advantage of MAP is that it is not expected to calcify, as it has been shown that the lack of strong ionic forces (i.e. the weak acidity of DOPA moieties) and of nucleating surfaces in these assemblies inhibits the growth of phosphate deposits in sea water, thus allowing MAP to maintain its strong adhesive nature (low glass transition temperature). In addition, the use of $Ca^{2-}$ ions in assemblies of mussel adhesive proteins will also contribute to the reversal of any $Ca^{2+}$ concentration gradient within the implant/tissue interphase. The reversal of the $Ca^{2+}$ concentration gradient, along with the weak acidity of DOPA moieties, should act as a further deterrent in $Ca_3(PO_4)_2$ build-up in the MAP membrane. Resistance to calcification is evaluated both in vitro (in DMEM culture medium) and in vivo (subcutaneously in rats).

Humic acids may also be polymerized, or self-assembled into a bioactive layer. Humic acids or "humic substances" are heterogeneous, high-molecular weight organic acids having a large proportion of DOPA, and are resistant to microbial degradation. The known ability of humic acids to donate and accept electrons from a variety of metals and organic molecules explains their capability to shuttle electrons between the humic-reducing microorganisms and the Fe(III)-Fe(II) oxide. It has been suggested that humic acids participate in a biological electron transfer as a result of the electron accepting ability of quinone moieties when reduced to hydroquinones and vice-versa. This renders the $Fe^{3+}$/humic acid assembled membranes an attractive vehicle for the attachment of various kind of cells to the bioactive layer.

Higher order supramolecular hydrogel architectures may be assembled on top of the MAP or humic acid layers, employing the well studied poly(anion)/poly(cation) technology. Suitable poly(anions) include the salts of poly (glutamic acid), and its copolymers with other amino acids. Suitable poly(cations) include the salts of polylysine, and its copolymers with other amino acids.

In another embodiment, the tissue-implant interface comprises more than one bioactive polymer layer. For example, a mussel adhesive protein layer may be first self-assembled onto the outer surface of the implant, followed by self-assembly of a (poly)anion/(poly)cation film. Alternatively, a NAFION™ layer may be disposed between the sensor and a hydrogel layer. NAFION™, being a low surface energy polymer, is generally nonadherent with other synthetic organic polymers when placed in an aqueous environment. Standard procedures to modify the surface of the fluoropolymer such as poly(tetrafluoroethylene) are accordingly used to produce a functional NAFION™ surface that can covalently bind another polymer layer. The most commonly used modifying agent is sodium (available commercially as Tetra-Etch), which produces unsaturated hydrocarbon chains at the NAFION™ surface. Bulk free radical polymerization of the unsaturated functional groups with the hydrogel monomers, e.g, results in adhesion to the NAFION™ surface.

Other components may also be incorporated into the bioactive polymer layer, such as poly(ethylene oxide) (PEG), to minimize protein adsorption. Poly(ethylene oxide) is most readily incorporated into the hydrogel, for example, by co-polymerization of a vinyl monomer having poly (ethylene oxide) side chains, for example poly(ethylene glycol) methacrylate (which is commercially available from Aldrich Chemical Co.), or a divinyl-terminated poly (ethylene glycol) macromonomer. Copolymerization of HEMA and poly(ethylene glycol) methacrylate in the presence of AIBN yields a more flexible, unhydrated copolymer. The optimal molecular weight and content of poly(ethylene oxide) for each application can be determined by protein adsorption studies.

To provide further chemical functionality on the bioactive polymer layer, particularly a hydrogel layer, either polyvinyl alcohol or polyethylene imine may be employed as macromolecular surfactants. Where hydroxyl functionalities are available, the coupling is promoted by tresylation. Poly (ethylene oxide) may also be grafted to hydroxyl groups on the surface of the polymer layer by tresylation coupling with Jeffamine, an amine-terminated poly(ethylene oxide) commercially available from Huntsman.

A further embodiment of the present invention is a tissue/implant interface consisting of an implant having an outer surface and a bioactive polymer, particularly one of the above-described hydrogels, MAP layers, or poly(anion)/poly(cation) layers disposed on the outer surface, wherein the presence of the bioactive polymer provides effective modification of the tissue response without use of an added tissue response modifier. In particular, use of one or more of these layers alone, is expected to improve the biocompatibility, lifespan, and/or function of the implant.

Where used, association of the tissue response modifiers with the bioactive polymer layer may be by physical means, i.e., entrapment within the polymer layer, or by covalent attachment within the bioactive polymer layer and/or at the surface of the bioactive polymer layer. Entrapment may occur at the time the layer is formed, or subsequently, i.e., by absorption of the tissue response modifier into the formed layer. By adjusting the degree of crosslinking of the layer, the rate of diffusion from the layer to the site of implantation can be controlled.

Covalent coupling, e.g., to the hydroxy functionality of the HEMA monomers in the hydrogel or hydroxyl moieties of the MAP protein, can be advantageous in that the bound factor can still bind to cell surface receptors and contribute to signal transduction, but does not leach from the hydrogel or be endocytosed. Coupling of peptides to hydroxyl functionalities may accomplished by known methods, for example by activation of the hydroxyl group of HEMA with tresyl chloride in the presence of triethylamine, followed by reaction with the N-terminus of the peptide. For the adhesive ligand REDV, the GREDVY (glycine-arginine-glutamic acid-aspartic acid-valine-tyrosine) motif is used. The glycine moiety acts as a spacer, while the tyrosine moiety enables radioiodine binding assays for determination of the coupling efficiency. Since the swelling ratios of the hydrogels are highly dependent on the solvent employed, appropriate choice of solvents allows control of the spatial distribution of the coupled factors. Use of a highly swelling solvent such as dimethyl sulfoxide allows homogeneous distribution of the factor(s) throughout the hydrogel, while use of a low-swelling solvent such as dioxane results in the factor(s) being more or less confined to the surface of the hydrogel.

In still another embodiment, the tissue response modifiers are present in the bioactive polymer layer as part of a controlled release delivery system. Use of controlled release delivery systems allows controlled, site specific delivery of the tissue response modifier to the implantation site, thus limiting biodegradation and reducing or eliminating systemic side effects, and improving the therapeutic response. Duration of action and dosage level are also adjustable, which is critical in controlling inflammation and fibrosis. Lower dosage levels are required for targeted delivery (as opposed to systemic administration), which lowers the cost of treatment.

Controlled release vehicles are known in the art, and most commonly comprise biodegradable linkages or forms which release the active agent upon degradation at the site of implantation. Exemplary controlled release vehicles include but are not limited to biodegradable polymers, nanoparticles, and controlled release vesicles such as liposomes and microspheres. Since many controlled release delivery systems can be manufactured to provide different release rates under the same conditions, in one embodiment, a single tissue response modifier may be provided at different release rates, to achieve a specific release profile. In another embodiment, the availability of a plurality of tissue response modifiers is regulated by the different release rates of the delivery systems.

Microspheres are particularly useful. Microspheres are micron-sized spherical articles, typically prepared using natural or synthetic polymers, and have been demonstrated to effectively deliver a number of drugs, including dexamethasone and various proteins. To maximize control of the diverse and dynamic processes involved in inflammation, repair, and neovascularization, mixtures of microspheres comprising different tissue response modifiers may be used in combination. Additionally, microspheres are manufactured so as to release the various tissue response modifiers at different rates, to control the different phases of the tissue reaction. Microspheres having diameters of greater than about 10 microns are presently preferred. The microspheres may be covalently attached to the implant or hydrogel, or be physically entrained within the hydrogel. Coupling to the interactive hydrogels is by incorporation of different functional surfactants onto the surface of the microspheres.

Microsphere delivery systems may be encapsulating, having the active agent incorporated into the center, or have the active agent dispersed throughout the polymer matrix. Each microsphere is optimized for formulation method, release rate, and dosage of specific tissue response modifiers. Co-polymer ratio, particle size and drug loading are varied to achieve desired release rates of the tissue response modifiers. Since small microspheres are likely to be phagocytosed and removed from the site, preferred microspheres have diameters in the range from about 10 to about 100 microns. The method described by M. Tsung and D. J. Burgess, in J. Pharm., Vol. 86, p.603 (1997) may be used for particle sizing. SEM, TEM, and optical microscopy are used to determine microsphere size, shape, surface characteristics, and internal structure.

A number of polymers are suitable for use in slow release microspheres, including but not being limited to proteins, as disclosed in U.S. Pat. No. 5,271,961, polyorthoesters, poly(lactic acid), poly(gycolic acid) polyahydrides, polyphosphazene, polycaprolactone, polyhydroxybutyrate and combinations thereof. A preferred polymer is poly(lactic-glycolic acid) ("PLGA"). PLGA is bioactive, does not itself result in any significant inflammatory reaction, can be manufactured to have different release rates, and is suitable for use with a variety of both water-soluble and water-insoluble drugs. PLGA microsphere preparations are commercially available under the trade name LUPRON-DEPOT® and are approved for use by the Federal Drug Administration (FDA) for parenteral administration. Ratio of glycolic acid to lactic acid, particle size, molecular weight of the polymer and drug loading are varied to achieve desired release rates of the tissue response modifiers.

Modification of the PLGA microsphere surface by tresylation allows covalent attachment of the microsphere to the hydroxyl groups of the hydrogel. Attachment of polyethyleneamine or polyvinyl alcohol to the microsphere surface occurs by addition of these elements during microsphere preparation. These elements to allow coupling to the interactive surface hydrogels. Copolymerization of PLGA with a small amount of glutamic acid (approximately 5%) also allows coupling of the microspheres with the hydrogels.

Coating or modifying the surface of the PLGA microspheres also allows adjustment of biocompatibility, biodegradation, and release rates. Glutamic acid imparts a negative charge on the surface of the microspheres, allowing self assembly with the polypeptides. As an alternative, polyethyleneamine, phosphatidic acid or phosphatidylinositol attached to the microsphere surface imparts positive, negative, and negative charges, respectively. These elements become attached to the microsphere surface by incorporating them during microsphere preparation.

Preparation of microspheres comprising water-insoluble tissue response modifiers such as dexamethasone relies on the hydrophobicity of these molecules. A simple oil/water emulsion technique is used, wherein the dexamethasone, e.g., is entrapped within the internal oil phase (PLGA/methylene chloride) of the emulsion and hence within the microspheres following solvent evaporation, as described by C. Grandfils, et al., in J. Biomedical Materials Research, Vol. 26, p. 467 (1992). In order to increase dexamethasone content within the microspheres, dexamethasone partitioning into the aqueous phase is reduced by changing the oil phase, e.g. a methylene chloride/acetone mixture is used in place of methylene chloride.

For hydrophilic tissue response modifiers such as VEGF and other polypeptides, a modification of a multiple emulsion technique described by Toguchi et al. in J. Pharm. Sci., Vol. 83, p. 636 (1994) is used, since polypeptides are generally water soluble and therefore must be entrapped in the internal water phase of a water/oil/water emulsion. This method ensures polypeptide entrapment within the PLGA microspheres following solvent evaporation. During entrapment of VEGF, addition of phosphatidyl choline (PC) as a surfactant and reduction in the temperature of preparation to 30° C. results in improved emulsion stability and hence VEGF content and activity following entrapment in the microspheres. Sucralfate, a protease inhibitor, may be added to preserve polypeptide activity in vivo. Rat serum albumin may also be added to facilitate release rates.

In addition to the above-described methods, general methods for the manufacture of the present tissue/implant interfaces will depend on the nature of the implant, the nature of the one more bioactive polymer layers, and the nature of the tissue response modifiers. The part of the implant to be coated may be cast or coated with, or dipped or immersed into a solution of monomer, followed by polymerization onto the implant. Alternatively, the implant may be coated by melting, dipping, casting, or coating with the polymerized monomer, followed by removal of a solvent (if present). Self-assembly type polymer coatings are generally assembled directly on the surface of the implant. The monomer or polymer solutions may comprise the tissue response modifier; thereby incorporating the modifier during deposition, or the tissue response modifier may be adsorbed into the layer after deposition The amount of tissue response modifier incorporated in the tissue response modifier-delivery device will vary depending on the particular tissue response modifier used, the desired therapeutic effect, and the time-span over which tissue response modifier delivery is desired. Since a variety of devices in a variety of sizes and shapes may be fashioned for control of a variety of tissue responses, the upper and lower limits will depend on the activity of the tissue response modifier(s) and the time span of release from the device desired in a particular application. Thus, it is not practical to define a range for the therapeutically effective amount of the tissue response modifier to include. While the bioactive polymer may assume almost any geometry, layers are generally preferred, being in the range from about 0.05 to about 5 mm thick, preferably from about 0.1 to about 1 mm thick.

Determination of the precise tissue/implant configuration and the quantity and form of tissue response modifier effective to control the tissue response at the site of implantation is within the abilities of one of ordinary skill in the art, and will depend on the particular site of implantation, the length of time that the implant is intended to remain in the body, and the implant itself. Exemplary implantation sites include, but are not limited to, parts of various systems such as the gastrointestinal tract, including the biliary tract, urinary tract, genital tract, central nervous system and endocrine system, and sites such as blood vessels, bones and joints, tendons, nerves, muscles, the head and neck, and organs such as the heart, lungs, skin, liver, pancreas, eye, blood, blood progenitors and bone marrow.

Exemplary implants include, but are not limited to, prostheses, such as joint replacements, artificial tendons and ligaments, dental implants, blood vessel prostheses, heart valves, cochlear replacements, intraocular lens, mammary prostheses, penile and testicular prostheses, and tracheal, laryngeal, and esophageal replacement devices; artificial organs such as heart, liver, pancreas, kidney, and parathyroid; and repair materials and devices such as bone cements, bone defect repairs, bone plates for fracture fixation, heart valves, catheters, nerve regeneration channels, corneal bandages, skin repair templates, and scaffolds for tissue repair and regeneration; and devices such as pacemakers, implantable drug delivery systems (e.g., for drugs, human growth hormone, insulin, bone growth factors, and other hormones), and biosensors. Implantable drug delivery systems are disclosed in U.S. Pat. Nos. 3,773,919, 4,155,992, 4,379,138, 4,130,639, 4,900,556, 4,186,189, 5,593,697, and 5,342,622 which are incorporated by referene herein. Biosensors for monitoring conditions such as blood pH, ion concentration, metabolite levels, clinical chemistry analyses, oxygen concentration, carbon dioxide concentration, pressure, and glucose levels are known. Blood glucose levels, for example, may be monitored using optical sensors and electrochemical sensors. Various UV, HPLC and protein activity assays are known or can be modified to provide quantitation of the release rates, concentration, and activity of the tissue response modifiers in vitro and in vivo.

Figure 1:
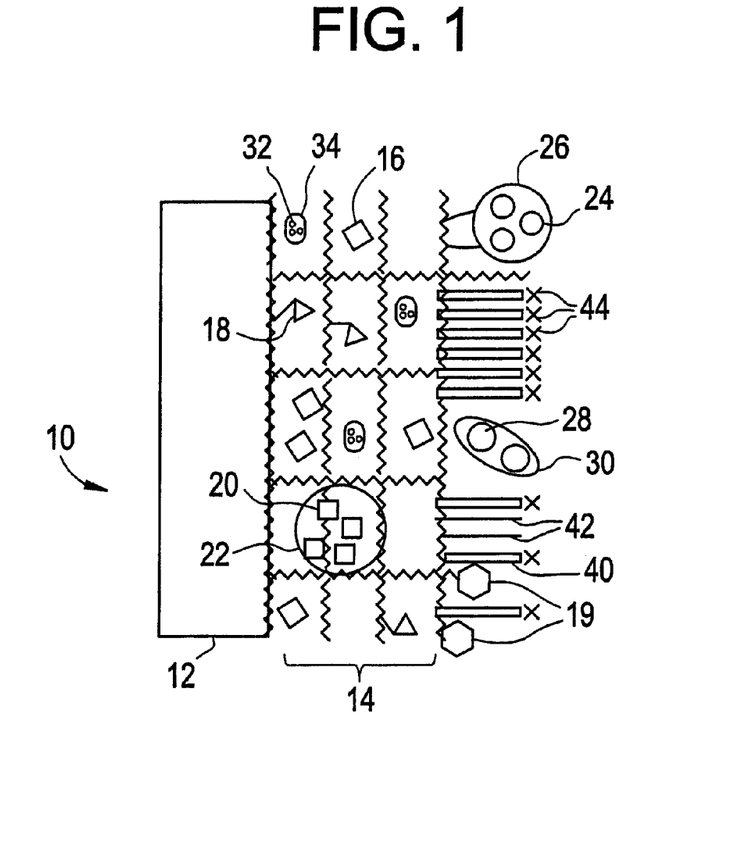
FIG. 1 is a schematic representation of an implant and tissue response modifier-hydrogel combination.

The above-described embodiments alone or in various combinations are all within the scope of the present invention. A schematic diagram of an exemplary tissue/implant interface 10 comprising an implant 12 and a hydrogel 14 is shown in FIG. 1. Tissue response modifiers 16 are entrapped within hydrogel 14, while tissue response modifiers 18 are covalently attached within hydrogel 14. The covalent attachments may be permanent, or hydrolysable. Tissue response modifiers 19 are associated with the surface of hydrogel 14, e.g., by ionic, hydrophilic, or hydrophobic interactions. Tissue response modifiers 20 are contained within microspheres 22, which are entrapped within hydrogel 14; tissue response modifiers 24 are contained within microspheres 26, which are covalently attached to hydrogel 14; and tissue response modifiers 28 are contained within microspheres 30, which are associated (by ionic or hydrophobic interactions, e.g.) with hydrogel 14. Tissue response modifiers 32 are contained within nanoparticles 34, which are entrapped within hydrogel 14. PEO chains 40 and PC chains 42 are covalently attached to the exterior surface of hydrogel 14. Adhesive ligands 44 are covalently attached to a plurality of PEO chains 40. In a further embodiment, one or more membrane layers may be disposed between implant 12 and hydrogel 14 (not shown). The membrane layers may advantageously be semi-permeable, allowing the diffusion of selected molecules to the implant surface. Inclusion of other bioactive agents in the tissue/implant interface having local or systemic effects (e.g., antibiotics, sedatives, hormones, anti-infectives, anti-fungals, analgesics, DNA, RNA, and the like) is also within the scope of the present invention.

Figure 2:
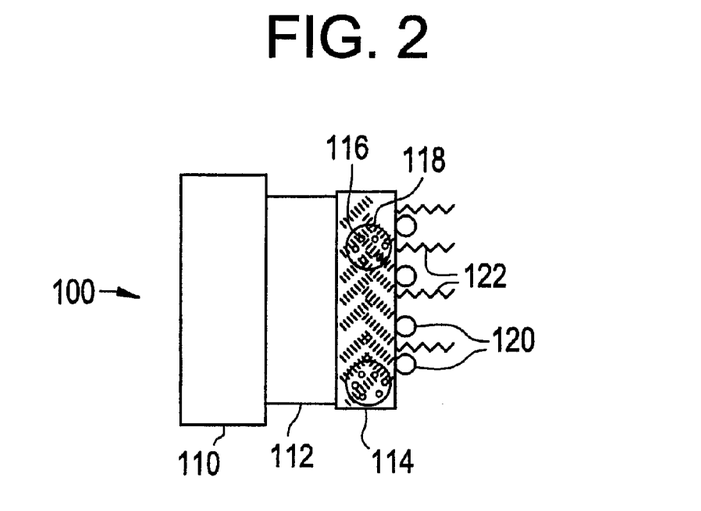
FIG. 2 is a schematic representation of an implant and tissue response modifier-MAP-poly(anion/polycation) combination.

A schematic diagram of an exemplary tissue/implant interface 100 comprising an implant 110, a mussel adhesive protein layer 112, and an alternating polycation/polyanion film 114 is shown in FIG. 2. Polycation/polyanion film 114 comprises tissue response modifiers 116 encapsulated by microspheres 118, which are entrapped within film 114. Tissue response modifiers 120 (e.g., VEGF) and adhesion ligands 122 are present external to polycation/polyanion film 114. PEO may be added to the assembly to control protein adhesion (not shown).

An exemplary application of the present invention is a stent used to keep the blood vessel open following balloon angioplasty, wherein at least a part of the outer surface of the stent comprises a bioactive polymer layer comprising microsphere-encapsulated drugs, e.g., Dexamethasone, to prevent the inflammatory response and excess tissue regeneration (restinosis). Such microspheres administered intravenously would be washed away by the rapid flow of blood.

Figure 3:
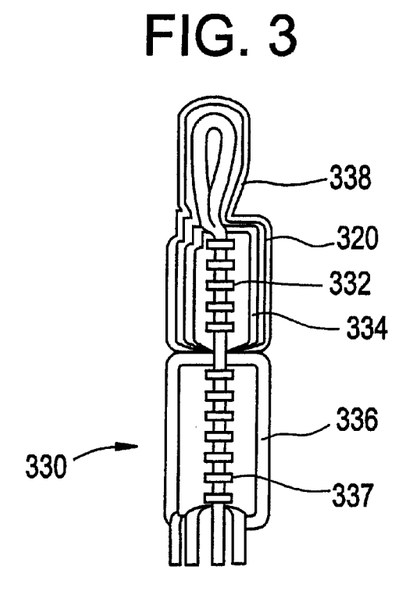
FIG. 3 is a schematic representation of a hydrogen peroxide-based amperometric sensor for monitoring subcutaneous levels of glucose and bioactive layer interface.

Another exemplary application of the above-described tissue/implant interface comprises an implantable electrochemical blood glucose sensor. Preferably, the electrochemical sensor monitors glucose concentration in subcutaneous tissue, using hydrogen peroxide-based amperometric detection. These sensors are highly specific for glucose, have a short response time, and may be readily miniaturized. As shown in FIG. 3, a preferred sensor 330 has a glucose-indicating (working) electrode 332 (the glucose-indicating electrode), and a reference-counter electrode 336. Working electrode 332 may comprise a coiled platinum wire 334, and reference electrode 336 may comprise a coiled silver/silver chloride wire 337. Glucose oxidase is immobilized in a matrix 338, for example bovine serum albumin/glutaraldehyde. In the presence of oxygen, glucose is oxidized by the enzyme, producing hydrogen peroxide ($H_2O_2$). The hydrogen peroxide is then oxidized at the surface of working electrode 334, thereby producing a measurable electric current, wherein the amount of current is proportional to the quantity of glucose present at the electrode. Sensor 330 has a linear response from zero to at least 20 millimolar (mM) glucose in vitro, with high sensitivity. Sensor 330 is about 0.5 mm in diameter, but may be made larger or smaller as the application dictates.

Figure 4:
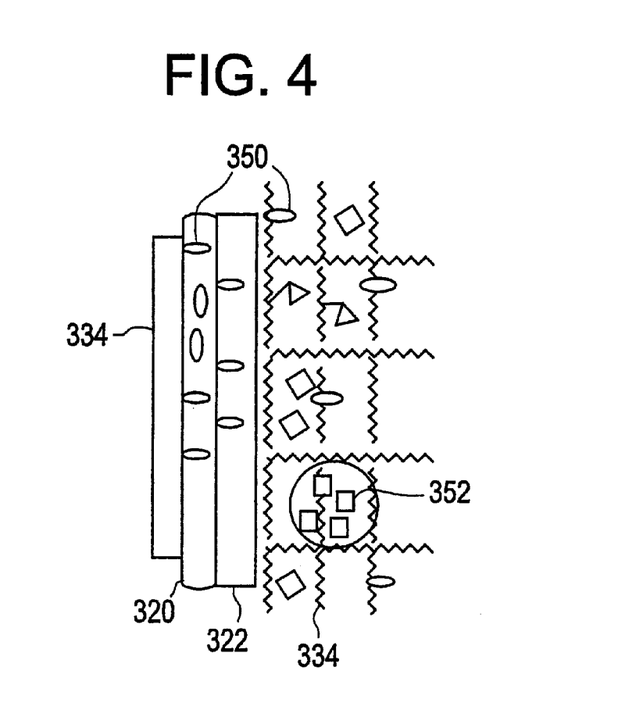
FIG. 4 is a detail of FIG. 3.

As shown in detail in FIG. 4, at least a portion of sensor 330 is protected from interaction with the surrounding tissue by the presence of a selectively permeable membrane. Platinum wire 334, for example, is coated with at least one selectively permeable membrane 320 for preventing or minimizing tissue interactions. An exemplary selectively permeable membrane is an electrodeposited poly(o-phenyldiamine) (PPD) film, which is permeable to hydrogen peroxide, but is impermeable to larger, interfering and/or degradative molecules such as ascorbic acid, uric acid, proteins, and the like.

The entire sensor 330 further comprises a first bioactive polymer layer 322, which further protects the sensor from interfering and/or degradative substances present in the tissue, such as proteins. As described above, an exemplary material is a perfluorinated ionomer membrane, e.g., NAFION™, which has been suitably modified to prevent calcification and other undesirable interactions. A second bioactive polymer layer 344, e.g., a hydrogel, is directly adjacent layer 322. Tissue response modifiers 350 are covalently bound to semipermeable membrane 320, first layer 322, and second layer 344. Tissue response modifiers 352 are also associated with second layer 344 in slow-release form to provide long-term delivery of the tissue response modifier to the site of implantation. Other glucose sensors are disclosed in U.S. Pat. No. 4,703,756, which is incorporated by reference herein.

The invention is further illustrated by the following non-limiting examples.

EXAMPLES

Example 1
Hydrogel Synthesis

Hydrogels of HEMA, FOSA and NVP (with a variety of monomer ratios) were polymerized using 0.1 mole % AIBN as a free radical initiator in bulk at 70° C. and in water/dioxane at 60° C. After 12–24 hours, crosslinked materials were obtained which were insoluble in water, acetone and a variety of other organic solvents. Residual monomer was removed by swelling in water/acetone followed by repeated rinsing. The degree of swelling depended on the relative weight percent (wt. %) of each monomers used to form the gel. The impact of hydrogel composition (wt. % based on total amount of monomers) on swelling was determined and the results are shown in Table 1.

TABLE 1

| Sample No. | HEMA | NVP | FOSA | PEG-Acrylate | Swelling* |
|---|---|---|---|---|---|
| 1 | 100 | 0 | 0 | 0 | 73 |
| 2 | 94 | 0 | 6 | 0 | 64 |
| 3 | 62 | 32 | 6 | 0 | 97 |
| 4 | 35 | 59 | 6 | 0 | 244 |
| 5 | 56 | 28 | 6 | 10 | 110 |
| 6 | 40 | 24 | 6 | 30 | 140 |

*average percent increase in weight after 14 hours in distilled $H_2O$ at 37° C.

These data indicate that only 5% incorporated FOSA monomer can decrease the swelling in distilled $H_2O$ by 10%. The addition of NVP monomer can increase the swelling to various amounts based on the charge ratio of the monomer. The incorporation of the PEG acrylate monomer can also effect the swelling properties while potentially decreasing protein adsorption. Data indicate that the proposed materials can be successfully prepared with as many as four co-monomers, and that they exhibit appropriate hydrogel properties that can be well controlled. These hydrogels also contain residual hydroxyl functionality that may be employed to covalently attach tissue response modifiers and/or slow release delivery systems using known procedures.

Example 2
Preparation of HEMA-FOSA Hydrogels

To prepare this gel, 2.45 g of HEMA (Aldrich, used as received), 15 g of FOSA ("FX-13" from 3M, recrystallized 3 times in methanol), 0.007 g AIBN (Aldrich, recrystallized in methanol) were mixed with the aid of 1.5 mL dioxane (Aldrich, used as received). This solution was poured into a Teflon mold which was then placed in an oven at 70° C. for 12 hours. The gel was then swollen in water and water/acetone mixtures to leach out unreacted monomer and linear (uncrosslinked) polymer. The resultant gel swollen to equilibrium in deionized water had a thickness of 1 mm. For permeability measurements, a circle of appropriate size (1.5 cm diameter) was stamped out of the gel.

Example 3
Determination of Permeability of HEMA-FOSA Hydrogels In vitro

Figure 5:
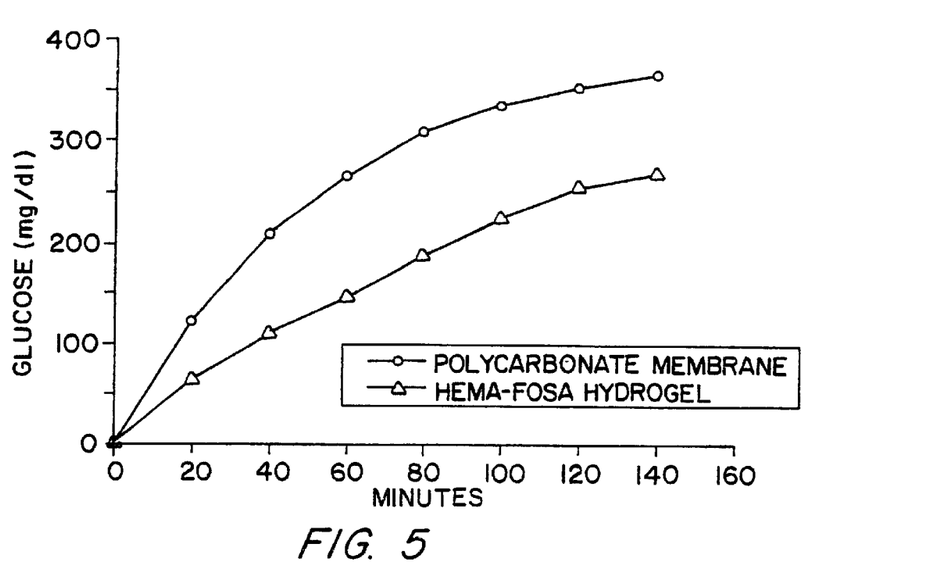
FIG. 5 is a graph showing the permeability of a HEMA-FOSA hydrogel to glucose.

To determine permeability of the new HEMA-FOSA hydrogels to glucose, the free-standing hydrogel film was supported by a 1.5 cm diameter polycarbonate membrane having 10-micron sized pores. The permeability of the HEMA-FOSA hydrogel to glucose is determined using a single-sided magnetic biodialyser (Sialomed Corp.). This device consists of a sample chamber having as opening which is covered with the supported HEMA-FOSA hydrogel. When the chamber top is screwed on, it secures the membranes in place, but does not cover the membranes. This entire apparatus is place into a beaker containing the dialysis buffer, and stirred at a fixed rate and temperature (37° C.). Over time, the content of the sample chamber diffuses into the buffer. The interior of the chamber is filled with 1 mL of 1M glucose in phosphate buffer solution (PBS), in PBS with physiologically relevant proteins (albumin, complement, fibrinogen, fibrin, and fibronectin), in cell culture medium, and in cell culture medium with cells (vascular endothelial cells and fibroblasts). The dialysis buffer (B) consists of 50 mL of the same solution, but without glucose. This high sample to buffer ratio ensures that the change in glucose concentration in the dialysis buffer over time is measurable. Samples (50 micro liters) of the dialysis buffer are collected at 20 minute intervals for 2 hours. The concentration of glucose in the dialysis buffer samples is quantified using a Beckman Glucose Analyzer II. Using this protocol, the permeability of the polycarbonate membrane (for reference), NAFION and HEMA-FOSA hydrogel is assessed, as shown in FIG. 5. Based on these data, use of the hydrogels should only slightly reduce the permeability to glucose because of the high water content of the materials.

Example 4

Preparation of VEGF-Poly(HEMA)

VEGF was incorporated into hydrogels comprising poly (HEMA) and sucralfate (a protease inhibitor) by incubating the hydrogel with 0.075 microgram/microliter of VEGF. The samples were then allowed to air dry for about 2 hours at room temperature.

An ELISA assay (R&D Systems, Minneapolis, Minn.) is used to quantify VEGF during bioactive layer or slow release delivery system preparation. To conserve VEGF (or other valuable tissue response modifier), release studies are conducted using a miniaturized, high throughput method, wherein tissue response modifier-microsphere samples are placed in 12 well plates with phosphate buffer (pH 7.4, 37° C.) and volumes are adjusted to maintain sink conditions. At appropriate time points, samples are removed and analyzed for tissue response modifier content. In addition, the in vitro release studies are conducted in the presence of 1) protein and 2) cells (leucocytes, vascular endothelial cells and fibroblasts) in attempt to mimic the in vivo environment at the implant/tissue interphase. VEGF activity is monitored by a cell proliferation assay in vitro as described by J. U. Muhlhauser et al., in Circulation Research, Vol. 77, p. 1077 (1995) and radioactivity monitoring using $^{125}$I-VEGF (new England Nuclear, Boston, Mass.) in vivo. Ultraviolet (UV) analysis and high pressure liquid chromatography (HPLC) assays are available to quantify dexamethasone concentrations in vitro and in vivo, respectively. Partition coefficient data may also be used to determine tissue response modifier distribution during preparation.

Example 5

VEGF-Induced Neovascularization in Rats

A simple hydrogel model of local drug delivery was used to demonstrate that the presence of VEGF at the implant/tissue interface will induce neovascularization in rats. Accordingly, the above-described VEGF-poly(HEMA) with sucralfate was subcutaneously implanted in Sprague-Dawley rats. To control for non-specific effects, hydrogels comprising poly(HEMA) and sucralfate (with no VEGF) were also implanted into Sprague-Dawley rats. Two weeks after implantation, the animals were sacrificed and the implantation sites were examined for neovascularization. An implant comprising poly(HEMA) and sucralfate, but without VEGF failed to induce any detectable vascularization. In contrast, implantation of the hydrogel comprising poly (HEMA), sucralfate, and VEGF induced massive neovascularization in the rat subcutaneous tissue. These data clearly demonstrate that use of angiogenic factors enhances the vasculature around an implant.

Example 6

Preparation and Characterization of NAFION™-$Fe^{3+}$ Self-Assemblies

NAFION™, a perfluorinated ion-exchange resin (5% w/v in lower aliphatic alcohol mixture and water; equivalent weight of 1100 g of polymer per mol of —$SO_3H$) and hexahydroferric chloride ($FeCl_3.6H_2O$) and ferric citrate were obtained from Aldrich. A.C.S. certified KCl was purchased from Fischer and used without further purification. 28–30 wt. % aqueous solution of $NH_4OH$ (Acros) and 35–38% hydrochloric acid (J. T. Baker) were used as a 1% dilution to adjust pH. Millipore quality deionized water (resistivity>18 M Ω) was utilized in all experiments.

Silicon wafers with native oxide (100 orientation) and microscope glass slides (Fisher) were used as substrates for the self-assembly. These were cleaned in pirahana solution ($H_2SO_4/H_2O_2$ (7:3)), rinsed with deionized water and methanol, kept in deionized water overnight and used for the self-assembly growth without further surface modification. 1 mg/mL ($9.09\times10^{-4}$M), based on the repeat unit molecular weight) NAFION™ solution was prepared by diluting the as received solution in a (9:1) methanol/water mixture and used for all experiments. The pH of these solutions was adjusted with aqueous $NH_4OH$ solution. In addition, the ionic strength of NAFION™ solutions was modified with KCl. 0.5 g of $FeCl_3.6H_2O$ was solubilized in 100 mL of water to produce 5 mg/mL (18.5 $10^{-3}$ M) solution. Similar ferric citrate solutions were also prepared, where the pH of these solution could be varied from 2–6 with slow addition of base. This greatly minimize $Fe^{3+}$ afflicted damage to the glucose oxidase enzyme.

An HMS™ Series Programmable Slide Stainer (Carl Zaiss, Inc.) was used for the layer-by-layer assembly of NAFION™ with $Fe^{3+}$. The sample holder in the HMS™ Series Slide Stainer was covered to reduce solvent evaporation particularly obvious around the substrate edges, thereby improving film quality. Each dip cycle consist of 8 steps. First the substrates were immersed in NAFION™ solution for 15 minutes followed by 3 consecutive washing step, of one minute each in Millipore quality deionized water. Subsequently, the substrates were dipped into ferric chloride solution for 15 minutes followed by three washes as before. 12 subsequent dip-cycles were usually employed in this study. The substrates were constantly agitated throughout the dip-cycle to improve film quality. After completion of a desired number of dip cycles the substrates were removed and rinsed with Millipore water and methanol and dried with air.

Solubility studies in a series of solvents have led to the conclusion that depending on the dielectric constant of the solvent or solvent mixture, NAFION™ forms either homogeneous mixtures, colloids or precipitates. Based on a 9/1 methanol/water solvent ratio used in this study (ε~38), NAFION™ is expected to attain a micellar conformation with the hydrophobic fluorocarbon backbone buried inside and the polar sulfonate groups located on the surface.

Figure 6:
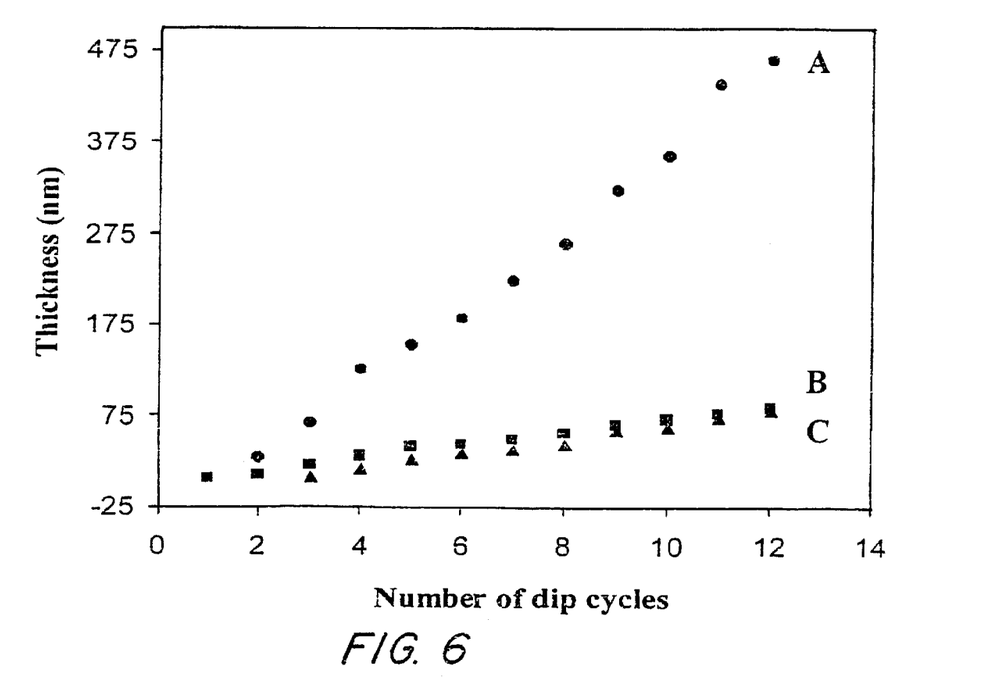
FIG. 6 is a graph showing ellipsometrically determined thickness versus dip cycle for alternating NAFION™/$Fe^{3+}$ assemblies as a function of the pH of NAFION™ solution; (A) pH=3, (B) pH=4.5, and (C) pH=5.5.

FIG. 6 illustrates the ellipsometrically determined film thickness as a function of number of dip cycles. Maintaining the pH of $FeCl_3$ and wash solutions constant, the pH of NAFION™ solution was found to have a profound influence in film growth. The fastest growth rate was observed at pH 3, corresponding to c.a. 40 nm per dip cycle. A abrupt transition in film growth is observed above pH of 4, leading to significantly lower deposition rates (i.e. 6.7 and 6.3 nm/dip-cycle for pH of 4.5 and 5.5 respectively).

Table 2 illustrates the hydrodynamic radius $R_H$ and diffusion coefficient $D_H$ of NAFION™ solutions as determined by dynamic light scattering (DLS).

TABLE 2

| | NAFION™ With 0.01 KCl | | NAFION™ Without KCl | |
|---|---|---|---|---|
| pH | $R_H$ (nm) | D (cm$^{-2}$s$^{-1}$) | $R_H$ (nm) | D (cm$^{-2}$s$^{-1}$) |
| 5.5 | 51.0 | $8.5 \times 10^{-8}$ | 115.9 | $3.75 \times 10^{-8}$ |
| 3.0 | 45.8 | $9.5 \times 10^{-8}$ | 113.5 | $3.83 \times 10^{-8}$ |

The influence of pH on the hydrodynamic radius of NAFION™ appears to be negligible for pH of 3 and 5.5. This concurs with the strong acidic character of sulfonate groups (NAFION's™ acidity —$H_o$ of about 12 in terms of Hammett acidity is comparable with 100% sulfuric acid) implying a nearly complete degree of ionization for both pH 3 and pH 5.5. On the other hand, the tendency of ferric ions to form insoluble hydroxides starts around pH greater than or equal to 4.3 based on solubility product of $Fe(OH)_3$ ($K_{sp}$ about $6 \times 10^{-39}$). This transformation of absorbed $Fe^{3+}$ to $Fe(RSO_3)_x(OH)_{1-x}$ results in increasing the basicity of the substrate. Based on these observations, the abrupt transition to lower growth rate of the NAFION™/$Fe^{3+}$ assemblies could be associated with neutralization-induced NAFION™ spreading.

Figure 7:
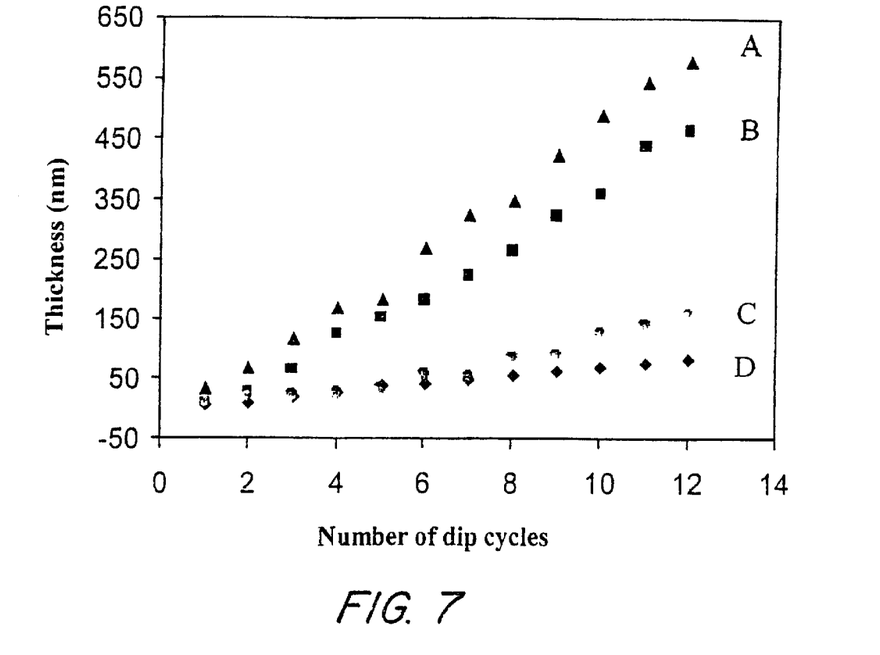
FIG. 7 is a graph showing ellipsometrically determined thickness versus dip cycle for alternating NAFION™/$Fe^{3+}$ assemblies as a function of the pH and ionic strength of NAFION™ solution; (A) pH=3, 0.01 M KCl; (B) pH—3, no salt; (C) pH=4.5, 0.01 M KCl; (D) pH—4.5, no salt.

FIG. 7 depicts film thickness of these assemblies as a function of the pH and ionic strength of NAFION™ solution. The addition of 0.01 M KCl was found to have a profound effect in the film growth rate. The influence of salt concentration on the thickness of the deposited films was also investigated, with the above value determined as optimum ionic strength based on film quality. At higher KCl concentrations i.e., 0.1 M, no film deposition was observed and salt was preferentially precipitating on the surface.

The well documented charge screening effect in polyelectrolytes, as a result of diminishing repulsive interactions between the negatively charged sulfonate groups, by addition of positively charged ions (i.e., $K^+$), allows NAFION™ to attain a more compact conformation. This results in nearly 60% reduction in hydrodynamic volume as compared to salt-free solutions (see Table 2). The comparable increase in diffusion coefficient of NAFION™ micelles imply greater diffusion rate on the assembly surface. Surprisingly enough, the average growth rate shown in FIG. 2A (pH 3. 0.01 M KCl), which is c.a. 47 nm/dip-cycle, corresponds roughly to the hydrodynamic radius shown in Table 1. This implies that surface adsorption is accompanied with minimum NAFION™ surface-spreading, relative to the no-salt case, where a nearly 65% spreading results in 40 nm/dip-cycle growth rate. The effect of salt appears to be equivalent for different pHs based on the relative strength of the surface-induced interactions that tend to flatten the micelle and charge-screening forces that try to keep it intact. It appears that at pH of 3, the latter is the dominant effect, with the case inversed for pH of 4.5, where the basicity of $Fe(RSO_3)_x(OH)_{1-x}$ overpower the charge-screening forces. This thermodynamic based model could, however be subject to certain kinetic imposed restrictions with respect to the rate of micelle arrival to the surface, as inferred by the larger diffusion coefficients in the presence of salt. EDAX of self-assembled NAFION™/$Fe_{3+}$ films, treated in DMEM nutrient mixture showed more than two orders of magnitude decrease in intensity of calcium line compared to NAFION™ films deposited by dip-coating.

Figure 8:
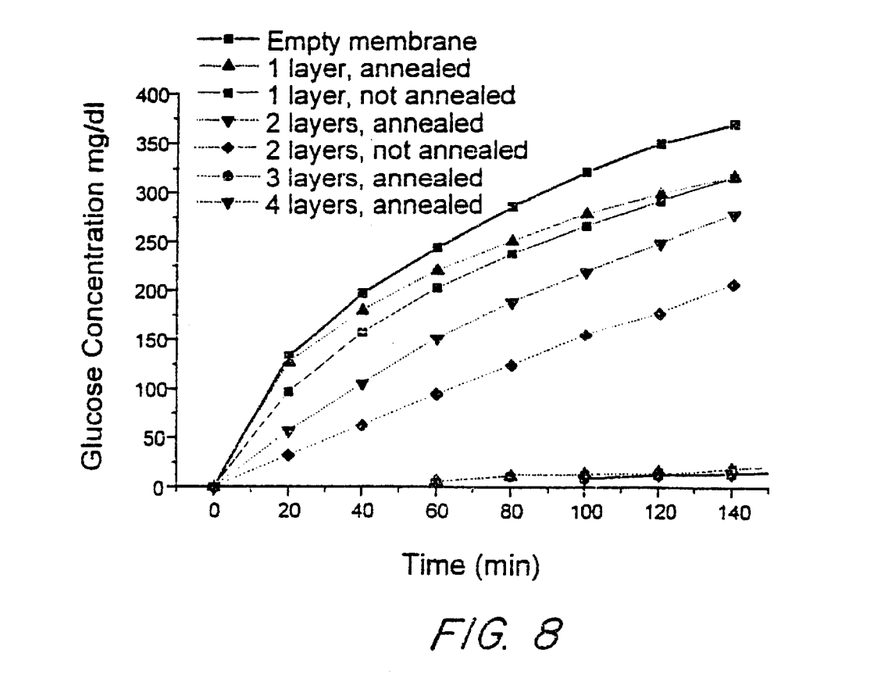
FIG. 8 is a graph showing glucose permeability data as a function of successive NAFION™/$Fe^{3+}$ self assembled monolayers on a 0.1 micron glass-fiber membrane.
Figure 9:
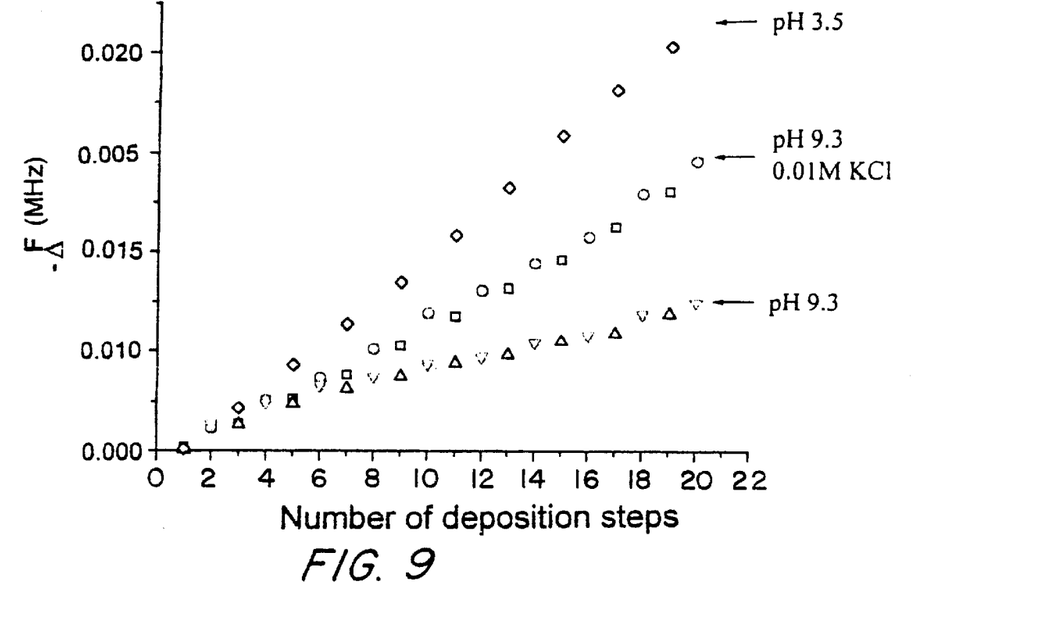
FIG. 9 shows Quartz Crystal Microbalance (QCM) frequency shifts (directly related with the mass deposited on the QCM sensor) versus dip cycle for humic acid/$Fe^{3+}$ assemblies, as a function of the pH and ionic strength of humic acid solutions.

FIG. 8 illustrate the glucose permeability data obtained with these assemblies on 0.1 micron glass fiber membranes.

Example 7

Preparation and Characterization of Humic Acid Self-Assemblies

Figure 10:
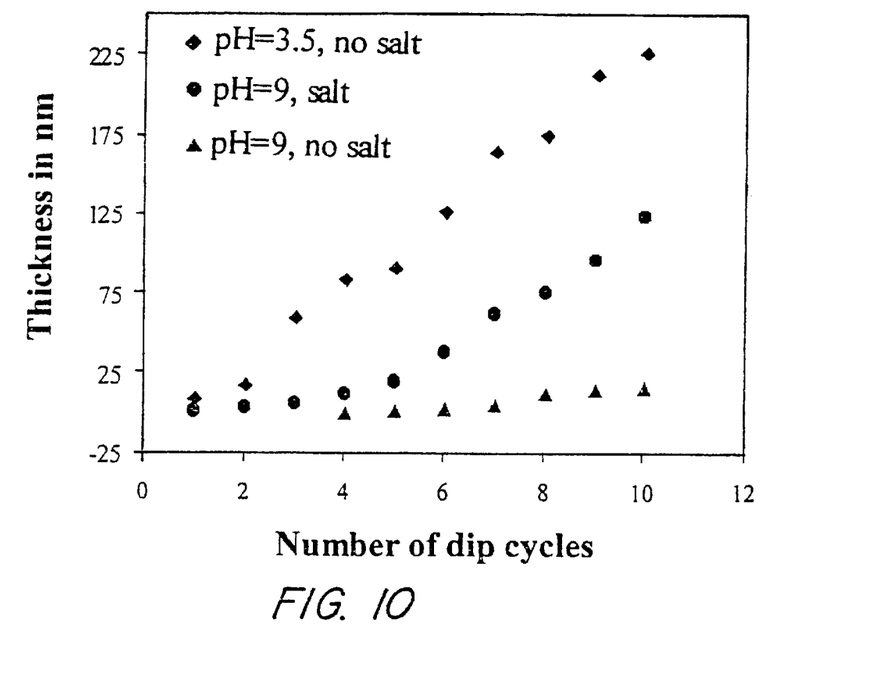
FIG. 10 is a graph showing ellipsometrically determined thickness versus dip cycle for humic acid/$Fe^{3+}$ assemblies, as a function of the pH and ionic strength of humic acid solutions.

Humic acid solutions were prepared (1 mg/mL concentration) by dissolving 1 g of humic acid (HA, used as obtained), sodium salt (obtained by Aldrich) in 1 L of deionized water. The pH of the resulting solution was found to be 9.3. The pH of the HA solution can be varied by addition of acid (e.g., HCl), thus greatly modifying the degree of ionization of carboxylic groups in HA and significantly affecting the molecular conformation of the polymer in solution. The resulting net thickness of the deposited film increases with decreasing pH due to the natural coiling up of the polyionic molecules as its degree of ionization decreases. A very similar effect is observed in the presence of salt. Salt induced charge screening effects allows attaining more compact coiled conformations at the same pH and thus consequently thicker films are formed. Quartz Crystal Microbalance (QCM) ( FIG. 4) and ellipsometric data (FIG. 10) support these observations.

Example 8

In Vitro Response to a Glucose Sensor Comprising a Bioactive Layer and Tissue Response Modifiers(s) (Prospective)

Function of the glucose sensor comprising a bioactive layer alone is assessed by incubating the sensors at 37° C. in PBS with and without physiologically relevant proteins (albumin, complement, fibrinogen, fibrin, and fibronectin, and the like, and in culture media with or without physiologically relevant cells (cells vascular endothelial cells, fibroblasts, and the like). All test buffers and culture media contain 5.6 mM glucose. The sensors are continuously polarized at +0.7 V. To test the sensors, increasing amounts of a sterile glucose is added, and the sensitivity (in nA/mM), the background current, and the response time of the sensors is determined. The effect of compounds such as ascorbic acid, uric acid, and acetaminophen, which are known to interfere with the response of glucose sensors, is also evaluated to select the sensor configuration that offers the best protection against electrochemical interferences.

Example 9

In Vitro Response to a Glucose Sensor Comprising a Bioactive Layer and Tissue Response Modifier(s) (Prospective)

Adsorption of key plasma and tissue proteins onto the implant surfaces and/or bioactive layers is evaluated using radioactive labeled proteins, for example albumin, the third component of Complement (C3) and fibrinogen/fibrin, and fibronectin. Once the general binding characteristics of these proteins are established, the ability of the same materials to activate the complement and coagulation pathways present in plasma is determined.

Determining in vitro which implant/bioactive layer/tissue response modifier configurations minimize fibroblast migration, proliferation and collagen synthesis, and maximize vascular endothelial cell proliferation and migration allows design of implant configurations that will be optimal in extending implant lifetime in vivo. Impact on fibroblast and vascular endothelial cell proliferation is quantified using the standard H³ Thymidine assay. Fibroblast synthesis of collagens (type III and type I) are quantified using hydroxyproline incorporation and ELISA assays. Fibroblast and vascular endothelial cell migration are determined using computer aided video microscopy and the microcarrier bead assay.

Example 10
In Vivo Tissue Response to of a Glucose Sensor (Control)

To characterize baseline tissue reactions, a glucose sensor without tissue response modifiers was constructed as shown in FIG. 1 at 10, comprising glucose-indicating (working) electrode 12 and a reference-counter electrode 16. Glucose oxidase was immobilized in a bovine serum albumin/glutaraldehyde matrix 18. Sensor 10 further comprised an outer membrane of NAFION, which is thermally conditioned at 120 or above to prevent in vivo degradation. The thermally annealed sensor showed a linear response up to at least 20 mM glucose and a slope of 3.2 nA/mM with an intercept of 5.7 nA. The response time of the sensor was about 30 seconds and the time required for the background current to decay to steady state after initial polarization was about 35 min. The sensor had a high selectivity for glucose, and a low partial pressure of $O_2$ affected the response of the sensor only for levels below 8 mm Hg.

The sensors were implanted in the back of dogs and were tested regularly over a 10 day period. About 45 minutes was required for the current to stabilize after polarization in vivo. After this period a bolus intravenous injection of glucose was made and the sensor output was monitored. Blood was periodically sampled from an indwelling catheter to determine blood glucose levels. A 5–10 minute delay was observed between the maxima in blood glucose and the sensor's signal, corresponding to the known lag time between blood and subcutaneous glucose levels. Although experiments with dogs showed that the response of some of the sensors remained stable for at least 10 days, others failed. This lack of reliability, which is common to all implantable glucose sensors developed worldwide, is believed to be mostly caused by the tissue reaction to the sensor. In addition, the sensors were implanted in Sprague-Dawley rats and tissue samples removed one day and one month after implantation. The specimens were processed for traditional histopathology using H&E staining, as well as trichrome staining) (fibrin and collagen deposition). At one-day post-implantation, a massive inflammatory reaction was observed at the tissue site around the sensor. The inflammatory reaction comprised primarily polymorphonuclear (PMN) and mononuclear leukocytes, as well as fibrin deposition. By one-month post-implantation, significant chronic inflammation and fibrosis were present at the tissue site around the sensor, together with mature collagen and fibroblasts, and loss of vasculature. The chronic inflammation seen at one month appeared to be lymphocytic in nature.

Example 11
In Vivo Response to Implantation of a Glucose Sensor Comprising a Bioactive Layer and Tissue Response Modifier(s) (Prospective)

Diabetes is induce in rats by intraperitoneal injection of streptozotocin (75 mg/kg) 10 days before an implantation, and monitored using test strips. Animals are also monitored daily for clinical symptoms of distress, and animals showing significant clinical distress are sacrificed. Sensors comprising a semipermeable membrane and a bioactive layer are implanted into the interscapular subcutaneous tissue of anesthetized normal and diabetic rats (250–300 g body weight). Two sensors per rat are implanted. To minimize tissue damage, the sensors are implanted through a thin wall needle (18 to 20 Gauge), and the needle is removed, leaving the sensor in place with the connecting leads exiting the skin. The leads are secured to the skin to prevent removal of the sensor.

Response of the sensors is tested on days 0, 3, 7, 14, 21, and 28. During each test, the rats are anesthetized, and then prior to administering glucose, the sensors are connected to a small potentiostat (Petit Ampere, BAS) and subjected to 0.7 V. The current produced by the sensor is either read directly on the digital display of the potentiostat or recorded on a small strip-chart recorder. After a "run-in-period" of about 1 hour to obtain a stable signal, a glucose solution (30% solution, 1.0 g/kg body weight) is injected intraperitonealy (I.P.). Plasma glucose concentration is determined in blood samples obtained from the tail vein using a heparinized Pasteur pipette. The concentration of glucose in the blood samples is measured using a Beckman Glucose Analyzer II. The glycemia of the rat is correlated with the current produced by the sensor. In vivo studies have demonstrated that plasma glucose increases to a plateau that lasts at least 10 minutes. This time interval is long enough to establish equilibration between plasma and subcutaneous glucose concentrations. By using the plasma glucose values and the corresponding current levels at both the basal state and the peak, an in vivo sensitivity coefficient (in nA/mM) and the extrapolated background current is determined.

To better assess the response time of the sensor an Intravenous Glucose Tolerance Test (IVGTT) is performed on some animals. For this test, before sacrificing the animal at the end of each 4 week study, a catheter is place in a jugular vein of the anesthetized rat, and glucose is rapidly injected intravenously (I.V.). The I.V. injection of glucose will allow for a better determination of the response time of the sensor since the change in glucose levels will be more rapid that the I.P. injection of glucose. The glycemia of the rat and the current produced by the sensor will be measured and correlated as above.

Additionally, tissues response modifier in vivo partitioning affects the pharmacokinetic (PK) data. Intravenous and sub-cutaneous solution PK data in normal and treated animal models (e.g., rats) are used to calculate local effective concentrations to control inflammation, fibrosis and neovascularization, and as a starting point to calculate microsphere drug loading and release rates. Solution PK data are necessary in deconvolution (mathematical separation) of microsphere PK data, as tissue response modifier PK often alters in the microspheres.

Accordingly, the subject implant and its associated hydrogel is implanted in normal and treated animals. A deconvolution, model-independent approach and the Wagner-Nelson method is used to analyze the plasma concentration time profiles. The response of normal animals to a subcutaneous implantation comprising a hydrogel and associated tissue response modifiers is investigated using standard histologic-based protocols.

Sensors that lose their function in vivo are explanted and the surrounding tissue removed. To determine the cause for failure, the explanted sensors are re-tested in vitro to evaluate their in vitro response. Some sensors are also used for surface analysis to determine chemical and physical changes of the sensor membranes and interactive hydrogels.

The addition of the various combinations of polymer/tissue response modifiers to implants provide an extremely simple, flexible and effective means to control the implant/tissue interface, improving implant lifetime and function. The close association of the tissue response modifiers overcomes the disadvantages of simple injection of the agent at the site of implantation, where blood flow or muscle movement alone can cause migration of the agent away from the site of implantation. For proteinaceous agents, which are particularly subject to degradation, the close association of the therapeutic agent with the implant can prevent significant loss of efficacy.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An implant having a tissue/implant interface, comprising an implant having an outer surface and a bioactive polymer layer self-assembled with metal cations, wherein the self-assembled polymer layer is adjacent to at least a portion of the outer surface, and wherein the self-assembled bioactive polymer layer provides at least one tissue response modifier to the site of implantation in a quantity effective to control tissue response at the site of implantation.

2. The implant of claim 1, wherein the tissue response modifier is provided in a controlled release form by nanoparticles, emulsions, liposomes, or microspheres.

3. The implant of claim 2, wherein the tissue response modifier is encapsulated within a microsphere, physically entrained within a microsphere, or covalently attached to a microsphere.

4. The implant of claim 1, wherein the tissue response is inflammation, fibrosis, fibroblast formation, fibroblast function, cell proliferation, neovascularization, cell injury, cell death, leukocyte activation, leukocyte adherence, lymphocyte activation, lymphocyte adherence, macrophage activation, macrophage adherence, thrombosis, neoplasia, protein adhesion to the implant, or a combination comprising at least one of the foregoing.

5. The implant of claim 1, wherein the tissue response modifier is an anti-fibrotic agent, steroidal anti-inflammatory agent, non-steroidal anti-inflammatory agent, antiproliferative agent, cytokine, cytokine inhibitor, growth factor, vascular growth factor, neutralizing antibody, adhesive ligand, hormone, cytotoxic agent, or a combination comprising at least one of the foregoing.

6. The implant of claim 1, comprising a tissue response modifier which affects inflammation.

7. The implant of claim 1, comprising a tissue response modifier which affects neovascularization.

8. The implant of claim 1, comprising first a tissue response modifier which affects inflammation and a second tissue response modifier which affects neovascularization.

9. The implant of claim 8, wherein the tissue response modifier is 2-(3-benzophenyl)propionic acid, 9-alpha-fluoro-16-alpha-methylprednisolone, methyl prednisone, fluoroxyprednisolone, 17-hydroxycorticosterone, cyclosporin, (+)-6-methoxy-α-methyl-2-naphthalene acetic acid, 4-isobutyl-α-methylphenyl acetic acid, Mitomicyin C, transforming growth factor alpha, anti-transforming growth factor beta, epidermal growth factor, vascular endothelial growth factor, anti-transforming growth factor beta antibody, anti-fibroblast antibody, anti-transforming growth factor beta receptor antibody, arginine-glycine-aspartic acid, REDV, or a combination thereof.

10. The implant of claim 1, wherein the tissue response modifier is covalently attached to the self-assembled bioactive polymer layer, is entrapped within the self-assembled bioactive polymer layer, is associated with an outer surface of the self-assembled bioactive polymer layer, or a combination thereof.

11. The implant of claim 1, wherein the self-assembled bioactive polymer layer is a synthetic polymer.

12. The implant of claim 1, wherein the self-assembled bioactive polymer layer further comprises covalently bound poly(ethylene oxide), phosphatidyl choline, polyvinyl alcohol, polyethylene imine, an adhesive ligand, or a combination thereof.

13. The implant of claim 1, wherein the self-assembled bioactive polymer layer is a mussel adhesive protein.

14. The implant of claim 1, wherein the self-assembled bioactive polymer layer is assembled from humic acid.

15. The implant of claim 1, wherein the self-assembled bioactive polymer layer is assembled from glutamic acid.

16. The implant of claim 1, wherein the metal cations are $Fe^{3+}$ or $Ca^{2+}$.

17. The implant of claim 1, wherein the site of implantation is the gastrointestinal tract, biliary tract, urinary tract, genital tract, central nervous system or endocrine system.

18. The implant of claim 1, wherein the site of implantation is at blood vessels, bones, joints, tendons, nerves, muscles, the head, the neck, or organs.

19. The implant of claim 1, wherein the implant is a material, a prosthesis, an artificial organ, a repair device, an implantable drug delivery system, or a biosensor.

20. The implant of claim 1, wherein the implant further comprises an additional bioactive polymer layer.

21. The implant of claim 20, wherein the additional bioactive polymer layer is a hydrogel.

22. The implant of claim 1, further comprising a bioactive polymer layer formed by the polymerization of 2-hydroxyethyl methacrylate, a fluorinated acrylate, acrylic acid, methacrylic acid, or a combination comprising one of the foregoing monomers with an ethylenically unsaturated co-monomer.

23. The implant of claim 22, wherein the bioactive polymer layer is formed by co-polymerization of 2-hydroxyethyl methacrylate with hydroxypropyl methacrylate, N-vinyl pyrrolidinone, 2-hydroxyethyl acrylate, glycerol methacrylate, n-isopropyl acrylamide, N,N-dimethylacrylamide, glycidyl methacrylate, or a combination thereof.

24. The implant of claim 22, wherein the bioactive polymer layer is formed by co-polymerization of 2-hydroxyethyl methacrylate, N-vinyl pyrrolidinone, and 2-N-ethylperflourooctanesulfanamido ethyl acrylate in the presence of EGDMA.

25. An implant having a tissue/implant interface, comprising an implant having an outer surface and a self-assembled poly(anion)/poly(cation) film, wherein the film comprises at least one poly(anion) layer and one poly(cation) layer, the film being adjacent to at least a portion of the outer surface, and wherein the film provides at least one tissue response modifier to the site of implantation in a quantity effective to control tissue response at the site of implantation.

26. The implant of claim 25, wherein the poly(anion) is poly(glutamic acid) or copolymers thereof, and the poly(cation) is poly(lysine) or copolymers thereof.

27. The implant of claim 25, wherein the tissue response modifier is provided in a controlled release form by nanoparticles, emulsions, liposomes, or microspheres.

28. The implant of claim 25, wherein the tissue response modifier is encapsulated within a microsphere, physically entrained within a microsphere, or covalently attached to a microsphere.

29. The implant of claim 25, wherein the tissue response is inflammation, fibrosis, fibroblast formation, fibroblast function, cell proliferation, neovascularization, cell injury, cell death, leukocyte activation, leukocyte adherence, lymphocyte activation, lymphocyte adherence, macrophage activation, macrophage adherence, thrombosis, neoplasia, protein adhesion to the implant, or a combination comprising at least one of the foregoing.

30. The implant of claim 25, wherein the tissue response modifier is an anti-fibrotic agent, steroidal anti-inflammatory agent, non-steroidal anti-inflammatory agent, anti-proliferative agent, cytokine, cytokine inhibitor, growth factor, vascular growth factor, neutralizing antibody, adhesive ligand, hormone, cytotoxic agent, or a combination comprising at least one of the foregoing.

31. The implant of claim 25, comprising a tissue response modifier which affects inflammation.

32. The implant of claim 25, comprising a tissue response modifier which affects neovascularization.

33. The implant of claim 25, comprising first a tissue response modifier which affects inflammation and a second tissue response modifier which affects neovascularization.

34. The implant of claim 25, wherein the tissue response modifier is 2-(3-benzophenyl)propionic acid, 9-alpha-fluoro-16-alpha-methylprednisolone, methyl prednisone, fluoroxyprednisolone, 17-hydroxycorticosterone, cyclosporin, (+)-6-methoxy-α-methyl-2-naphthalene acetic acid, 4-isobutyl-α-methylphenyl acetic acid, Mitomicyin C, transforming growth factor alpha, anti-transforming growth factor beta, epidermal growth factor, vascular endothelial growth factor, anti-transforming growth factor beta antibody, anti-fibroblast antibody, anti-transforming growth factor beta receptor antibody, arginine-glycine-aspartic acid, REDV, or a combination thereof.

35. The implant of claim 25, wherein the tissue response modifier is covalently attached to the self-assembled bioactive polymer layer, is entrapped within the self-assembled bioactive polymer layer, is associated with an outer surface of the self-assembled bioactive polymer layer, or a combination thereof.

36. The implant of claim 25, wherein the self-assembled poly(anion)/poly(cation) film further comprises covalently bound poly(ethylene oxide), phosphatidyl choline, polyvinyl alcohol, polyethylene imine, an adhesive ligand, or a combination thereof.

37. The implant of claim 25, wherein the implant further comprises a hydrogel.

38. The implant of claim 25, further comprising a bioactive polymer layer formed by the polymerization of 2-hydroxyethyl methacrylate, 2-hydroxyethyl methacrylate, fluorinated acrylates, acrylic acid, and methacrylic acid, and combinations thereof with ethylenically unsaturated co-monomers.

39. The implant of claim 38, wherein the bioactive polymer layer is formed by co-polymerization of 2-hydroxyethyl methacrylate with hydroxypropyl methacrylate, N-vinyl pyrrolidinone, 2-hydroxyethyl acrylate, glycerol methacrylate, n-isopropyl acrylamide, N,N-dimethylacrylamide, glycidyl methacrylate, and combinations thereof.

40. The implant of claim 38, wherein the self assembled bioactive polymer layer is formed by co-polymerization of 2-hydroxyethyl methacrylate, N-vinyl pyrrolidinone, and 2-N-ethylperflourooctanesulfanamido ethyl acrylate in the presence of EGDMA.

41. The implant of claim 25, wherein the site of implantation is the gastrointestinal tract, biliary tract, urinary tract, genital tract, central nervous system or endocrine system.

42. The implant of claim 25, wherein the site of implantation is at blood vessels, bones, joints, tendons, nerves, muscles, the head, the neck, or organs.

43. The implant of claim 25, wherein the implant is a material, a prostheses, an artificial organ, a repair device, an implantable drug delivery system, or a biosensor.

* * * * *